United States Patent [19]

Dyke

[11] 4,136,693
[45] Jan. 30, 1979

[54] CONSTANT FLOW I.V. DEVICE

[75] Inventor: Denis G. Dyke, Edinboro, Pa.

[73] Assignee: Johnson & Johnson, New Brunswick, N.J.

[21] Appl. No.: 795,579

[22] Filed: May 10, 1977

[51] Int. Cl.² ............................................. A61M 5/16
[52] U.S. Cl. ............................... 128/214 C; 137/177;
137/454; 137/576; 222/129; 222/189
[58] Field of Search ............ 128/214 R, 214 C, 214.2,
128/227; 222/129, 189; 137/453, 454, 576, 571,
197, 177

[56] References Cited

U.S. PATENT DOCUMENTS

| 2,664,085 | 12/1953 | Ryan | 128/214 C |
| 3,340,871 | 9/1967 | Jellies | 128/214 C |
| 3,929,157 | 12/1975 | Serur | 137/453 |
| 3,963,024 | 6/1976 | Goldowsky | 128/214 R |
| 4,013,072 | 3/1977 | Jess | 128/214 C |
| 4,030,495 | 6/1977 | Virag | 128/214.2 |

FOREIGN PATENT DOCUMENTS

| 1096431 | 2/1955 | France | 128/214 C |
| 817387 | 7/1959 | United Kingdom | 128/214 C |
| 1182016 | 2/1970 | United Kingdom | 128/214 C |

Primary Examiner—Dalton L. Truluck
Attorney, Agent, or Firm—Robert J. Baran

[57] ABSTRACT

This invention relates to a novel apparatus useful for the gravity fed delivery of a liquid from a first liquid reservoir to a second liquid reservoir. This apparatus is especially useful for the administration of intravenous (I.V.) solutions, where a constant flow, despite varying conditions of pressure in said second fluid reservoir (i.e. the blood-stream of the patient) is desirable if not absolutely required. The instant novel apparatus includes an upper chamber, means for passing said liquid from said first liquid reservoir to said upper chamber, means for maintaining a predetermined volume of said liquid in said upper chamber, said predetermined volume being less than the total volume of said upper chamber, thereby providing a non-liquid containing volume in said upper chamber, a lower chamber, first fluid communication means between said predetermined volume of liquid and said lower chamber, operable to pass said liquid from said upper chamber to said lower chamber, means for passing said liquid from said lower chamber to said second liquid reservoir, which include a port operably sealed by a filter which, when wet, will pass said liquid, but will not pass gases therethrough, and second fluid communication means between said non-liquid containing volume and said lower chamber. In a preferred embodiment, the instant novel apparatus comprises contiguous chambers, the bottom wall of said upper chamber forming the top wall of said lower chamber, and said first fluid communication means include a valve operable to regulate the flow of liquid therethrough. In this preferred embodiment, said second fluid communication means may be operably sealed by a valve, e.g. a filter valve, which passes gases but not liquids therethrough.

14 Claims, 4 Drawing Figures

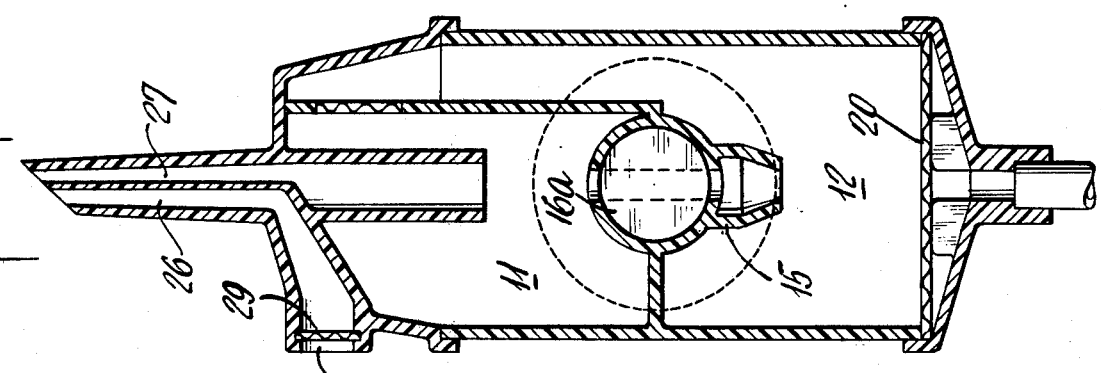
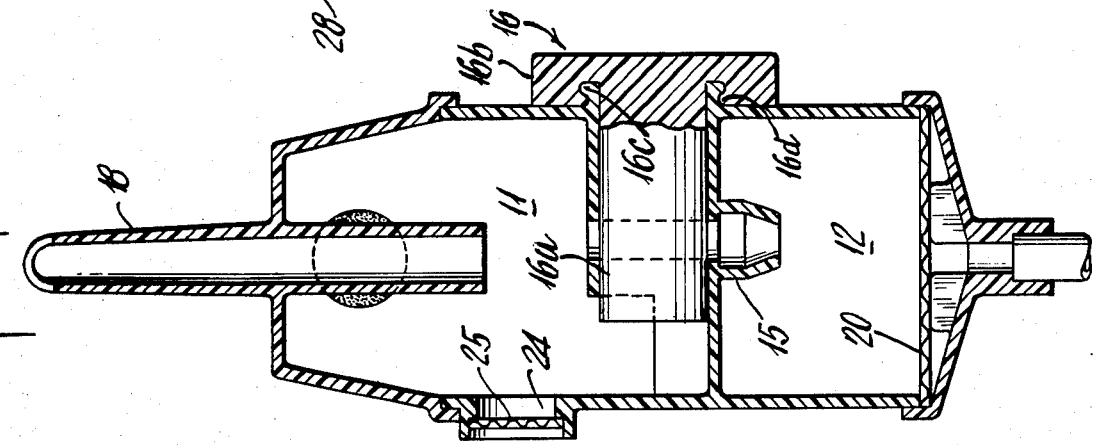
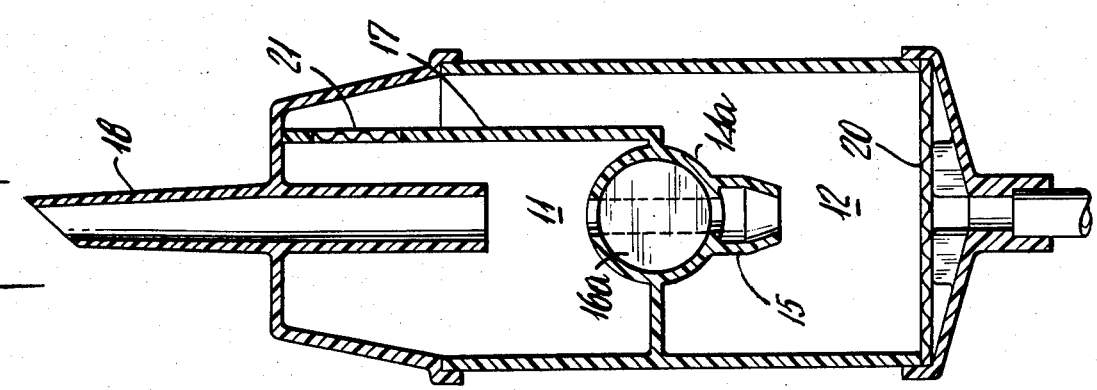
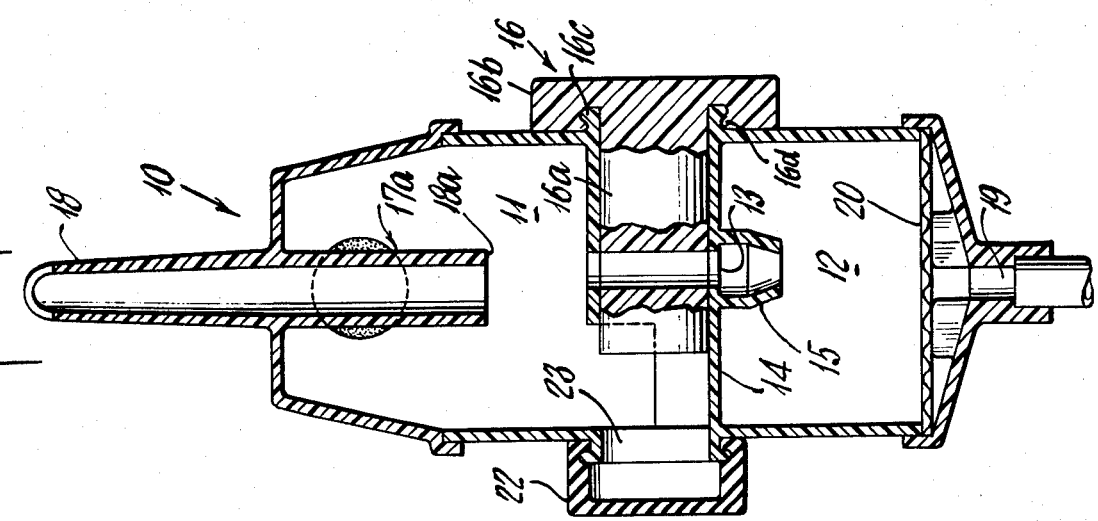

CONSTANT FLOW I.V. DEVICE

FIELD OF INVENTION

This invention relates to a novel apparatus useful for the gravity fed delivery of a liquid from a first liquid reservoir to a second liquid reservoir. This apparatus is especially useful for the administration of intravenous (I.V.) solutions, where a constant flow, despite varying conditions of pressure in said fluid reservoirs (as well as the means for passing said liquid between said reservoirs and the instant novel apparatus) is desirable if not absolutely required. In one embodiment of the instant invention, the novel apparatus is nonvented, therefore, when the first liquid reservoir is a collapsible bag, nonvented liquid delivery may be obtained.

BACKGROUND OF THE PRIOR ART

Apparatus, useful for the gravity fed delivery of liquids from one fluid reservoir to another, are known in the art. One example of applications, wherein an apparatus of this type is useful, is in the administration of I.V. solutions to a patient. In this particular use certain features such as maintaining uniform flow over fluctuating fluid reservoir pressures, monitoring the flow rate, and restricting the passage of air through the apparatus to the patient are very important. Additionally, non-vented operation (to eliminate contamination from the air) is desirable.

The prior art devices available for use in this application include the drip chamber described in U.S. Pat. No. 3,664,339. This device includes an upper chamber, a lower chamber and fluid communication means including valve means to provide adjustable fluid flow therebetween. This device is similar to the device of the instant invention in that both have an upper and lower chamber with fluid communication means therebetween however, unlike the instant novel device, the device described in this patent does not provide for uniform flow over varying fluid reservoir pressures. Uniform flow is effected in the instant novel apparatus by including a second fluid communication means between said chambers which allows passage of air but not liquid, thus equalizing the pressure in said chambers. Furthermore, the instant novel apparatus includes a filter valve prior to the exiting of the liquid to the patient. This filter valve is operable when wet to pass liquid but not air therethrough, thus metering the solution and preventing a possible air embolism as well as providing a final filtration of any particulate matter in the liquid.

U.S. Pat. No. 3,521,635 discloses a flow meter de-aerator for use in the administration of parenteral fluids. The apparatus disclosed therein has an upper and lower chamber and a single conduit in communication therebetween. This conduit provides for transfer of either liquid or air between said chambers. When used as an airway the purpose is to force air from the lower chamber into the upper chamber and thereby drive the liquid from said upper chamber into an upwardly extending shaft to dislodge air bubbles from a float device. During use, in the administration of I.V. solution, however, the conduit is filled with said liquid and therefore does not function as an airway. Furthermore, like the device described in U.S. Pat. No. 3,664,339 above, there is no filter provided nor any other valve means prior to the solution exit from the lower chamber. U.S. Pat. Nos. 3,664,339 and 3,776,229 disclose additional examples of other, two chamber, fluid transfer devices having a single conduit therebetween. As with the device described in saids U.S. Pat. No. 3,521,635, obtaining uniform flow over fluctuating fluid reservoir pressures is not possible with devices of this design.

In U.S. Pat. No. 3,929,157, a gravity fed, fluid delivery system is disclosed which includes upper and lower chambers, which are disposed so that the lower chamber receives fluid from said upper chamber via a fluid conduit therebetween; means for maintaining the fluid level in said upper chamber; and vent means which provides communication between said chambers, as well as the outside.

This system, similarly to the system described in U.S. Pat. No. 3,931,818 below, provides a float valve at the liquid exit from the lower chamber. This system, thus suffers the same disadvantages as the system described in that patent.

In U.S. Pat. No. 3,931,818, a non-vented liquid administration system is disclosed which comprises a sump chamber and a float chamber, wherein said chambers are connected by liquid communication means and a pressure equalizing air tube. This device differs from the instant novel device in that float valve means are provided prior to the exit of said liquid from said float chamber. The instant novel apparatus eliminates the possibility of mechanical failure inherent in valves of this type by use of a filter valve which also provides the feature of a final filtration, noted above. Furthermore, float valves require a certain minimum liquid level in said float chamber in order to bouy up the valve member and allow the exiting of liquid. The instant novel apparatus does not require any minimum liquid level in the lower chamber and, in fact, there is no liquid volume maintained above the filter valve in the lower chamber. A device similar to that disclosed in U.S. Pat. No. 3,931,818 is described in U.S. Pat. No. 3,963,024.

In U.S. Pat. Nos. 3,149,758 and 3,631,654, the use of filter valves is described. Nowhere, however, do said patents teach, disclose or suggest the use of said filter valves in the non-vented, gravity fed delivery of liquids from one fluid reservoir to another. These references, however, are hereby incorporated by reference for the purpose of disclosing hydrophobic and hydrophilic filter valves, useful in the apparatus of the instant invention.

SUMMARY OF THE INVENTION

The instant novel apparatus a housing which includes an upper chamber; means for passing said liquid from said first liquid reservoir to said upper chamber; means for maintaining a predetermined volume of said liquid in said upper chamber, said predetermined volume being less than the total volume of said upper chamber, thereby providing a non-liquid containing volume in said upper chamber; a lower chamber; first fluid communication means between said predetermined volume of liquid and said lower chamber, operable to pass said liquid from said upper chamber to said lower chamber; means for passing said liquid from said lower chamber to said second liquid reservoir, which include a port operably sealed by a filter which, when wet, will pass said liquid, but will not pass gases therethrough said means for passing said liquid from said lower chamber to said second fluid reservoir, i.e. a patient further including liquid collecting means below said filter having a finite volume and capable of maintaining said liquid level flush with said filter, said first fluid communication means, i.e. liquid communication means passing said droplets into contact with said filter prior to said droplets contacting said liquid level; and second fluid communication means between said non-liquid containing volume and said lower chamber. In a preferred embodiment, the instant novel apparatus comprises contiguous chambers, the bottom wall of said upper chamber forming the top wall of said lower chamber, and said first fluid communication means include a valve operable to regulate the flow of liquid therethrough. In this preferred embodiment, said second fluid communication means may be operably sealed by a valve e.g. a filter valve, which passes gases but not liquids therethrough.

This invention may be more easily understood by reference to FIGS. 1, 2, 3 and 4 which disclose preferred embodiments of the instant invention. In FIGS. 1, 2, 3 and 4 a two chambered I.V. administration device (10) is disclosed.

BRIEF DESCRIPTION OF THE DRAWINGS

FIG. 1 is a longitudinal, cross sectional view of a preferred embodiment of the instant novel device.

FIG. 2 is a cross sectional view of the device of FIG. 1 rotated 90° in a plane perpendicular to the plane of FIG. 1.

FIG. 3 is a longitudinal, cross sectional view of an alternate, preferred embodiment of the instant novel device having different priming means than the device of FIGS. 1 and 2.

FIG. 4 is a longitudinal, cross sectional view of an alternate, preferred embodiment of the instant novel device having vent means included therein, whereby when used in conjunction with a non-flexible (rigid), non-vented first fluid reservoir, such as an I.V. bottle, separate vent means are not required.

This device comprises an upper chamber (11) and a lower chamber (12) with first fluid communication means (13) therebetween. In this preferred embodiment, the chambers are contiguous, the bottom wall (14) of the upper chamber forming the top wall of the bottom chamber. Said first fluid communication means comprises a conduit through said bottom wall allowing fluid communication between said chambers. In the embodiments of FIGS. 1, 2, 3 and 4, this conduit may include drop forming means (15) which thereby allows the introduction of liquid into the bottom chamber in the form of droplets. Thus the flow of liquid through the instant novel device can be determined by "counting" droplets in a manner similar to the I.V. devices of the art.

Variable flow control means (16) are operably associated with said first fluid communication means. Said variable flow control means comprises a valve which is operable to vary the flow of liquid between said upper and lower chambers continuously between no flow and the flow approximately equal to that of the conduit itself.

The valve is made up of a stem (16a) and a knob (16b) having a circumferential groove (16d). The valve is rotatably engaged by a cylindrical fitting (14a) which is integrated with bottom wall (14) and may most clearly be discerned in FIGS. 2 and 3. The knob is press fit over engaging lip (16c) which is an extension of cylindrical fitting (14a) through the side wall of upper chamber (11), whereby groove (16d) holds the valve in operating relationship with first fluid communication means (15).

Said variable flow control means may include means for directly determining the flow rate operably associated therewith. For example, the valve described may include a numbered scale (not shown) whereby the flow through the conduit may be read by the positioning of the valve in relation to the conduit. In this alternate preferred embodiment drop forming means (15) can be eliminated since the flow of liquid may be read directly from the numbered scale. Of course, the instant novel device may include both drop forming means and a numbered scale for determining flow.

A second fluid communication means (17) is provided between said upper and lower chamber which in FIGS. 1, 2, 3 and 4 is a conduit passing through the bottom wall of said upper chamber. In this embodiment the conduit terminates at a point (17a) in said upper chamber which is near the top, but above point (18a). Means for passing said liquid from said first liquid reservoir (not shown but which may be a vented bottle or a collapsible air bag containing an I.V. solution) to said upper chamber is also provided. In FIGS. 1, 2, 3 and 4 said means (18) comprises penetrant means such as a hollow spike having a conduit extending from its uppermost portion therethrough to its termination (18a) in said upper chamber. In FIGS. 1, 2, 3 and 4 said conduit terminates at a point substantially below the termination of said second fluid communication means.

The lower chamber includes a port (19) located substantially at the lowest point thereof. The port is operably sealed by a filter (20) which is operable when wet to pass liquid but not air therethrough.

Means for providing fluid communication between said lower chamber and said second fluid reservoir are also provided. When the instant novel device is used in an I.V. administration system, said means will include an infusion tube, means for operably securing said infusion tube to said port, and a hollow needle for insertion into the vein of a patient, operably secured to said infusion tube.

A second filter valve (21) may be provided in association with said second fluid communication means which is operable to allow the passage of air but not said liquid therethrough.

Filters having the above characteristics are available from various manufacturers such as Nuclepore Corporation, Pleasanton, California; Gelman Instrument Co., Ann Arbor, Michigan; and Millipore Corporation, Bedford, Mass.

The device of the instant invention includes priming means. Said priming means are operable to draw liquid from said first liquid reservoir into said upper chamber and to displace the air therefrom. In one embodiment of the instant invention, said priming means may comprise a flexible member associated with said upper chamber and operable to reduce the volume of said upper chamber by means of pressure thereon. In the embodiment of FIGS. 1 and 2 said priming means include a rubber bulb (22), the interior of which is connected with said upper chamber through a port (23). The bulb can be squeezed to force air from the interior thereof, through said upper chamber into the first fluid reservoir. The release of pressure on the bulb causes a partial vacuum, drawing liquid from said first fluid reservoir into said upper chamber. Alternatively, the upper chamber may be fabricated from a resilient material such as polyvinylchloride. In this embodiment, the priming operation, i.e. forming a partial vacuum in said upper chamber, is principally the same.

It should be noted that the embodiment of FIGS. 1 and 2, when used in conjunction with a flexible, first fluid reservoir, such as an I.V. solution containing bag is capable of non-vented operation. This embodiment eliminates the danger of atmospheric contamination of the I.V. solution during use.

In the embodiment of FIG. 3, said priming means comprises a port (24) located in a side wall of said upper chamber which is operably sealed by a filter (25) which allows the passage of air but not liquid therethrough. In this embodiment, liquid will flow, via gravity, from said first fluid reservoir through said penetrant means into said upper chamber. The liquid will continue to rise displacing air from said chamber until the liquid level is above said port. At this point, the air remaining in the upper chamber will not be displaceable and the liquid will stop rising. Because of the hydrophobic nature of this filter, the port is effectively sealed when fluid is against it, thereby providing non-vented liquid delivery.

In the embodiment of FIGS. 1 and 2 wherein a flexible member is utilized as priming means, the liquid level will rise up to the point at which the termination of the conduit (18a) is covered. It will be noted that in both embodiments, as well as the embodiment of FIG. 4, discussed further below, the liquid level will remain constant during use since in neither case can more air be displaced. The instant invention thus provides means for maintaining a predetermined volum of liquid in said upper chamber. For purposes that will be disclosed further below, it is important that this predetermined volume be less than the total volume of said upper chamber thereby providing a non liquid containing volume or air space in said uppr chamber. This air space will be in communication with the lower chamber through said second fluid communication means.

FIG. 4 illustrates a third preferred embodiment of the instant invention. In this embodiment, the hollow spike (18) is partitioned into two separate conduits, said conduits being an airway (26) and a liquid passage (27). The airway is in commuunucation with the atmosphere through a port (28) located in a sidewall of said upper chamber but is not in fluid communication with the upper chamber itself. This port (28) is preferably sealed by a filter (29) which is operable to pass air but not liquid therethrough. This embodiment does not required separate venting means when used in conjunction with a structurally rigid first liquid reservoir such as an I.V. bottle. As the liquid flows from said first liquid reservoir, through liquid passage (27), into the upper chamber, a pressure differential is created which acts to draw air, through said airway, into said bottle. The pressure differential is sufficient to drive any liquid, which may flow into the airway during the initial penetration of the I.V. bottle by the hollow spike, back into the bottle. As the liquid flows from the I.V. bottle into the upper chamber, air will continue to be drawn through said airway to equalize the pressure and maintain the flow.

As described previously in relation to the other preferred embodiments, the volume of liquid in said upper chamber will continue to rise until no additional air can be displaced. Similarly to the embodiment of FIGS. 1 and 2, the liquid level will rise only until the termination of conduit 18a is covered, therefore, providing a predetermined volume of liquid in said upper chamber.

During use, the liquid will flow, from said first reservoir into said upper chamber to a predetermined volume. The liquid will pass from said upper chamber into said lower chamber via said first fluid communication means. The flow of said liquid may be regulated by means of said variable flow control valve.

The valve means allows adjustment of the flow to whatever flow rate is suitable for the intended use of the instant novel device. The liquid passes from said upper chamber into said lower chamber and exits from said lower chamber through a port located substantially at the bottom thereof.

The port in said lower chamber is operably sealed with a filter which passes the liquid but not air there through.

The filter, when wet, maintains the pressure equilibrium between the instant device and the fluid head of the first fluid reservoir. As each drop of liquid exits the instant device, a pressure drop occurs drawing liquid from said first fluid reservoir into the upper chamber and thereby maintains the equilibrium. Each drop of liquid that contacts the filter immediately wicks through and thus passes from the lower chamber into the means which provide fluid communication between said lower chamber and said second fluid reservoir. Because said means will have a finite volume, an equal volume of liquid is permitted to pass into said second fluid reservoir, while the filter holds the remaining liquid in check. Thus, the instant novel device does not respond to pressure generated by vertical movement of said first or second fluid reservoir or pressure changes therein. Rather so long as there is at least a minimal gravity vector summation force downward, the flow through the instant novel device is completely independent of said pressure changes.

When the instant novel apparatus is used in I.V. administration, the second fluid reservoir is the circulatory system of the patient. As stated above, in this application the port will be operably connected with a hollow needle by means of infusion tubing therebetween.

In this application, the filter provides the important feature of eliminating the concern that air might pass through the instant novel device to the patient. It will be appreciated by those skilled in the art that this is very desirable, in that the possiblity of an embolism is minimized.

The construction of the instant novel device will be apparent to those skilled in the art by reference to the above figures and disclosure.

What is claimed :

1. An apparatus for gravity fed delivery of a liquid from a liquid reservoir to a patient which comprises a housing including an upper chamber, means for passing said liquid from said liquid reservoir to said upper chamber, means for maintaining a predetermined volume of said liquid in said upper chamber, said predetermined volume being less than the total volume of said upper chamber, thereby providing a non-liquid containing volume in said upper chamber, a lower chamber, liquid communication means between said predetermined volume of liquid and said lower chamber, operable to pass said liquid from said upper chamber to said lower chamber in the form of droplets, means for passing said liquid from said lower chamber to said patient which include a port operably sealed by a hydrophilic filter which will pass said liquid, but will not pass gases therethrough, said means for passing said liquid from said lower chamber to said patient, further including liquid collecting means below said filter having a finite volume and capable of maintaining said liquid level flush with said hydrophilic filter, said liquid communication means passing said droplets into contact with said hydrophilic filter prior to said droplets contacting said liquid level and fluid communication means between said non-liquid containing volume and said lower chamber.

2. An apparatus according to claim 1 wherein said fluid communication means are operable to pass gases but not said liquid therethrough.

3. An apparatus according to claim 1 wherein said chambers are contiguous, said upper chamber having a bottom wall which also forms a lower chamber top wall.

4. An apparatus according to claim 3 wherein said upper chamber includes a top wall and said means for passing said liquid from said liquid reservoir to said upper chamber comprises a hollow spike having a conduit extending from its uppermost portion therethrough to its termination within said upper chamber, said hollow spike passing through said top wall.

5. An apparatus according to claim 3 wherein said communication means comprises conduit means extending from said upper chamber, through said bottom wall into said lower chamber, said conduit means also including valve means operable to vary the flow of said liquid through said conduit means.

6. An apparatus according to claim 4 wherein said fluid communucation means comprises an airway extending from said upper chamber, through said bottom wall into said lower chamber.

7. An apparatus according to claim 6 wherein said airway comprises a conduit including an opening located above the termination of said conduit of said hollow spike.

8. An apparatus according to claim 7 wherein said airway is sealed by a filter valve which is operable to pass air but not said liquid.

9. An apparatus according to claim 8 wherein said filter valve is positioned across the opening of said airway in said upper chamber.

10. An apparatus according to claim 3 wherein said upper fluid chamber includes priming means, operable to draw liquid from said liquid reservoir into said upper chamber, and to displace air therefrom.

11. An apparatus according to claim 10 wherein said priming means comprises a flexible member associated with said upper chamber and operable to reduce the volume of said upper chamber by means of pressure thereon.

12. An apparatus according to claim 10 wherein said upper chamber includes side walls, and said priming means comprises a port located in said side walls, said port being operably sealed with a filter which is operable to pass air but not said liquid.

13. An apparatus according to claim 4 wherein said upper chamber includes side walls and said hollow spike is partitioned into two separate conduits, one of said conduits being an airway, in communication with the atmosphere through a port located in said side walls but not in fluid communication with the upper chamber itself.

14. An apparatus according to claim 13 wherein said airway is sealed by a filter which is operable to pass air but not liquid therethrough.

* * * * *

UNITED STATES PATENT AND TRADEMARK OFFICE
CERTIFICATE OF CORRECTION

PATENT NO. : 4,136,693

DATED : January 30, 1979

INVENTOR(S) : Denis G. Dyke

It is certified that error appears in the above-identified patent and that said Letters Patent are hereby corrected as shown below:

In Column 2, line 4, "in saids U.S." should read -- in said U.S. --.

In Column 5, line 28, "predetermined volum" should read -- predetermined volume --.

In Column 5, line 33 "said uppr" should read -- said upper --.

In Claim 5, line 2, "communication" should read -- liquid communication --.

Signed and Sealed this

Sixteenth Day of October 1979

[SEAL]

Attest:

RUTH C. MASON
Attesting Officer

LUTRELLE F. PARKER
Acting Commissioner of Patents and Trademarks